United States Patent [19]

Hohmann

[11] 3,963,762

[45] June 15, 1976

[54] PROCESS FOR PRODUCING 1,5-DINITROANTHRAQUINONE AND 1,8-DINITROANTHRAQUINONE

[75] Inventor: Walter Hohmann, Leverkusen, Germany

[73] Assignee: Bayer Aktiengesellschaft, Leverkusen, Germany

[22] Filed: Oct. 10, 1974

[21] Appl. No.: 513,907

[30] Foreign Application Priority Data

Oct. 13, 1973 Germany............................ 2351590
Aug. 16, 1974 Germany............................ 2439280

[52] U.S. Cl. ............................................... 260/369
[51] Int. Cl.$^2$......................................... C07C 49/68
[58] Field of Search ................................... 260/369

[56] References Cited
UNITED STATES PATENTS 3,818,052   6/1974   Hohmann et al. ................... 260/369

FOREIGN PATENTS OR APPLICATIONS 2,248,704   4/1973   Germany

OTHER PUBLICATIONS

Kirk–Othmer Encyclopedia of Chemical Technology, vol. 2 (2nd Ed.), 1964 pp. 491–492.

*Primary Examiner*—Arthur P. Demers
*Attorney, Agent, or Firm*—Burgess, Dinklage & Sprung

[57] ABSTRACT

Substantially pure 1,5- and/or 1,8-dinitroanthraquinone is recovered from dinitration mixtures which may contain sulfuric acid or a perfluoralkane sulfonic acid by adjusting the nitric acid concentration in the nitration mixture to a value of 91 to 96% for a ratio by weight of nitric acid to solids of from 2.5 : 1 to 10 : 1; separating off the insoluble crude 1,5-dinitroanthranthraquinone at 15° to 50°C; taking up the 1,5-dinitroanthraquinone with 90 to 100% nitric acid in a ratio by weight of nitric acid to solids of from 0.5 : 1 to 3.5 : 1; stirring at 15° to 80°C; separating off the insoluble pure 1,5-dinitroanthraquinone thus obtained; adjusting the mother liquid left following separation of the crude 1,5-dinitroanthraquinone to a nitric acid concentration of from 88 to 94% for a ratio by weight of nitric acid to solids of from 3.0 : 1 to 12 : 1, with the proviso that the nitric acid concentration is at least 1.5% lower than in the preceding separation of crude 1,5-dinitroanthraquinone; and separating off the pure 1,8-dinitroanthraquinone obtained in this way at a temperature in the range of from 20° to 50°C and freeing it from the nitric acid adhering thereto.

16 Claims, No Drawings

PROCESS FOR PRODUCING 1,5-DINITROANTHRAQUINONE AND 1,8-DINITROANTHRAQUINONE

BACKGROUND

This invention relates to a process for recovering substantially pure 1,5- and/or 1,8-dinitroanthraquinone from dinitration mixtures.

It is known that the dinitration of anthraquinone produces mixtures consisting essentially of 1,5-, 1,8-, 1,6- and 1,7-dinitroanthraquinone. The separation of these mixtures has already been described in the literature, cf. DT-OS 2,143,253 (in oleum), Helv 14, 1404 (in monohydrate) and DT-OS 2,248,704 (in high-boiling organic solvents).

Unfortunately, these processes are unsatisfactory in terms of quality and/or yield, or on account of the large quantities of solvent required, or because production and separation have to be carried out in separate stages.

All these separation processes only yield a 1,5-dinitroanthraquinone which still contains at least 4.5 to 5 % by weight of 1,8-dinitroanthraquinone.

However, the presence of 1,8-dinitroanthraquinone in 1,5-dinitroanthraquinone in quantities as large as this is a troublesome factor in the production of products derived therefrom, for example the industrial-scale products 1,5-diaminoanthraquinone and 1-amino-5-benzoylamino-anthraquinone. Thus, all the 1,8-isomer remains in the 1,5-diaminoanthraquinone in the form of 1,8-diaminoanthraquinone after reduction. In the case of monobenzoylation, it remains in the 1-amino-5-benzoylamino anthraquinone in the form of 1-benzoylamino-8-aminoanthraquinone or 1,8-dibenzoylamino anthraquinone. So 1,8-substituted by products are extremely difficult and expensive to remove, in addition to which its removal involves heavy losses. If the 1,8-isomeric secondary products are not removed, their presence has an adverse effect in the production of dyes from 1-amino-5-benzoylamino anthraquinone by impairing the yields and/or colours and/or fastness. Accordingly, substantially complete removal of the 1,8-dinitroanthraquinone from 1,5-dinitroanthraquinone is of considerable commercial significance and is a problem to which, hitherto, there has been no economic solution.

Similarly, there has hitherto been no commercially and economically practicable process for the production of pure 1,8-dinitroanthraquinone. It is known that the commercially very important α,α-dinitration products of anthraquinone can be obtained in particularly high yields by nitration in concentrated nitric acid. Since the quantity of nitric acid required for this process is not appreciably higher than the quantity of sulphuric acid required for dinitration in $H_2SO_4$, nitric acid is economically superior to dinitration in sulfuric acid. The much simpler regeneration of the solvent is another factor in favour of nitric acid. According to Moiseva (Org.Polyprod, i. Krasitel, Moscow 1969, No. 4, 70–79), it is possible by the nitric acid process to obtain a 1,5-dinitroanthraquinone in a yield of 30 % of the theoretical amount. However, it is not possible under the conditions quoted by Moiseva (98 % $HNO_3$, 24 hours at 24°–25°C) to obtain pure 1,5-dinitroanthraquinone. Instead the products obtained still contain at least 5 % of 1,8-dinitroanthraquinone (cf. Example 18 below). Even under more stringent conditions (filtration under suction at elevated temperature, increasing the quantity of nitric acid used for washing), we were unable to obtain 1,5-dinitroanthraquinone with a purity of more than 95 % in a yield of more than 20 % of the theoretical amount. In addition, it is subsequently no longer possible to isolate pure 1,8-dinitroanthraquinone from the mother liquors, because they then contain too much 1,5-dinitroanthraquinone.

It has now been found that both pure 1,5-dinitroanthraquinone and also pure 1,8-dinitroanthraquinone can be isolated in good to very good yields from dinitration mixtures of anthraquinone by fractionation from nitric acid. In the context of the invention, dinitration mixtures are mixtures which consist essentially of 1,5- and 1,8-dinitroanthraquinone and which may additionally contain 1,6-, 1,7-, 2,6- and 2,7-dinitroanthraquinones or hydroxy dinitroanthraquinones and, to a small extent, other compounds which may even be free from nitro groups, such as anthraquinone. In general, the mixtures used as starting material will contain more than 50 % and preferably more than 60 % of 1,5- and 1,8-dinitroanthraquinone. The ratio of 1,5-dinitroanthraquinone to 1,8-dinitroanthraquinone can vary within wide limits and is by no means critical. In general, the mixtures used will have a ratio by weight of 1,5- to 1,8-dinitroanthraquinone of from 5 : 95 to 95 : 5. The proportion of ratio to one another of the aforementioned dinitroanthraquinones which may optionally be present in these dinitration mixtures consisting predominantly of 1,5- and 1,8-dinitroanthraquinones is also not critical and can vary within wide limits.

The process according to the invention enables 1,5- and/or 1,8-dinitroanthraquinone to be obtained in pure form from dinitration mixtures of this kind, irrespective of how these dinitration mixtures have been obtained. For example, dinitration mixtures which have been obtained in known manner by the direct nitration of anthraquinone or 1-nitroanthraquinone, or mixtures of anthraquinone or 1-nitroanthraquinone can be used in the same way as, for example, dinitration mixtures which have been obtained by nitration of the secondary products accumulating during the purification of 1-nitroanthraquinone. It is also possible to use dinitration mixtures which have been obtained by mixing any products, solutions or suspensions of any origin which contain 1,5- and 1,8-dinitroanthraquinone. It is preferred to use dinitration mixtures of the kind obtained as reaction mixtures in the direct nitration of anthraquinone with concentrated nitric acid, optionally in the presence of strong acids, such as sulphuric acid or perfluoralkane sulphonic acids, such as perfluormethane or perfluorbutane sulphonic acid which may be used in a quantity of up to 20 % by weight, based on nitric acid. The reaction mixture thus obtained may be purified in accordance with the invention without any need for the reaction products to be further worked up, optionally after previous adjustment of the nitric acid concentration required for carrying out the process according to the invention, for example by distilling off concentrated nitric acid and/or by adding water or aqueous nitric acid.

In the process according to the invention, a crude 1,5-dinitroanthraquinone still containing about 5 to 30 %, preferably 8 to 15 %, of 1,8-dinitroanthraquinone is initially separated off and purified by treatment with highly concentrated nitric acid. Pure 1,8-dinitroanthraquinone is subsequently separated off from the mother liquors of the crude 1,5-dinitroanthraquinone.

1,5-Dinitroanthraquinone may be obtained in pure form independently form 1,8-dinitroanthraqinone. Thus, it is possible by the process according to the invention to prepare either only 1,5-dinitroanthraquinone without subsequently isolating the 1,8-dinitroanthraquinone, or to separate only 1,8-dinitroanthraquinone from dinitration mixtures without previously isolating the 1,5-dinitroanthraquinone. However, it is generally only advantageous to do this in cases where one of the two compounds to be separated is present in a large excess in a dinitration mixture of the kind in question. However, it is only possible to isolate pure 1,8-dinitroanthraquinone, without previously separating crude 1,5-dinitroanthraquinone, from mixtures of the kind which contain no more than 15% of 1,5-dinitroanthraquinone.

The invention provides a commercially advantageous method of obtaining 1,5- and 1,8-dinitroanthraquinone in yields and purities which, hitherto, it has not been possible to obtain in their isolation from nitric acid. In the case of 1,5-dinitroanthraquinone, the purity amounts to around ≥ 97% and, in the case of 1,8-dinitroanthraquinone, to ≥ 98%.

The process according to the invention is carried out by adjusting in the dinitration mixture used a nitric acid concentration of from 91 to 96 %, preferably from 92.5 to 95.5 %, and a ratio by weight of nitric acid to solids of from 2.0 : 1 to 10 : 1, preferably from 2.5 : 1 to 10 : 1, at temperatures in the range of from 15° to 50°C, preferably from 20° to 35°C; separating off the insoluble crude 1,5-dinitroanthraquinone which still contains about 8 to 30 % of 1,8-dinitroanthraquinone, preferably after stirring for 1 to 15 hours; optionally washing it with 30 to 80 % by weight of 90 to 100 %, preferably 98 % nitric acid; subsequently treating the crude 1,5-dinitroanthraquinone with 90 to 100 %, preferably 98 to 100 % nitric acid in a ratio by weight of nitric acid to solids of from 0.5 to 3.5 : 1, preferably from 1 to 2 : 1; stirring the mixture for ½ to 40 hours at 0°C to boiling temperature, more especially at 20° to 70°C; and separating off the insoluble pure 1,5-dinitroanthraquinone, optionally washing it with 95 to 100 %, preferably with 98 % nitric acid, followed by working up using methods known per se. In the context of the invention, the solids content is the total content of nitration products in the dinitration mixture used. This solids content is determined by methods known per se, generally by pouring part of the dinitration mixture into ice-water and then filtering the precipitate obtained under suction and washing it until neutral, followed by drying.

Pure 1,8-dinitroanthraquinone is separated off from the mother liquor of the crude 1,5-dinitroanthraquinone by adjusting a nitric acid concentration of from 88 to 94 % and a ratio of nitric acid to solids of from 3.0 : 1 to 12 : 1, preferably from 3.5 : 1 to 10 : 1, at temperatures in the range of from 20° to 50°C, and freed from the nitric acid adhering to it by methods known per se, the nitric acid concentration being adjusted in such a way that it is at least 1.5 % lower than in the preceding separation of 1,5-dinitroanthraquinone. Pure 1,8-dinitroanthraquinone obtained in this way only contains from 0.2 to 0.6 % of 1,5-dinitroanthraquinone. The yields of pure 1,5-dinitroanthraquinone amount to between 28 to 34%, and the yields of pure 1,8-dinitroanthraquinone to as much as 23 % of the stoichiometric yield.

In the separation of pure 1,5-dinitroanthraquinone, followed by the separation of 1,8-dinitroanthraquinone, it has proved to be advantageous either to separate the 1,5-dinitroanthraquinone at a nitric acid concentration of from 94 to 96 % and with a ratio by weight of nitric acid to solids of from 5.5 : 1 to 3.5 : 1 and, accordingly, to separate 1,8-dinitroanthraquinone at a nitric acid concentration of from 91 to 93 % and with a ratio by weight of nitric acid to solids of from 7 : 1 to 3.5 : 1, or alternatively to separate the 1,5-dinitroanthraquinone at a nitric acid concentraton of from 91 to 93 % and with a mixing ratio of nitric acid to solids of from 9.5 : 1 to 6.5 : 1 and, accordingly, to separate 1,8-dinitroanthraquinone at a nitric acid concenration of from 88 to 91 % and with a ratio by weight of nitric acid to solids of from 12 : 1 to 7 : 1. Accordingly, high acid concentrations correlate with high solids contents, whilst low acid concentrations correlate with low solids In cases where nitration is carried out in nitric acid, the precipitation conditions for pure 1,8-dinitroanthraquinone can be adjusted, for example, by adding water or aqueous nitric acid, preferably with a concentration of greater than 65 %, or by distilling off nitric acid. For example, the nitration of anthraquinone with 5.5 to 12 parts by weight, preferably with 6 to 9 parts by weight, of 98 % nitric acid is best carried out by distilling off 15 to 35 % by weight and preferably 23 to 28 % by weight of 98 to 100 % nitric acid (based on the total weight of the mother liquor from the separation of the crude 1,5-dinitroanthraquinone) from the nitration mixture, preferably under reduced pressure at 50° to 70°C, followed by stirring after cooling, for example for 2 to 5 hours at 25° to 30°C. To establish the precipitation conditions by adding water, water is added at 20° to 70°C in a quantity of 20 to 27 ml per 100 g of anthraquinone used, or alternatively a nitric acid of corresponding water content is added. The addition is best accompanied by brief heating to 60° to 75°C until a clear solution is obtained, followed by stirring after cooling. quantity By distilling off more nitric acid or by adding more water, optionally in the form of aqueous nitric acids, it is possible to obtain from the mother liquor of the pure 1,8-dinitroanthraquinone other defined fractions, for example a highly pure 1,5-and 1,8-dinitroanthraquinone mixture which contains less than 3 % of 1,6- and 1,7-dinitroanthraquinone. To this end, the mother liquor remaining after separation of the 1,8-dinitroanthraquinone may be concentrated by distilling off nitric acid to between 70 and 90 % and preferably to between 75 and 85 % of its original weight. Alternatively the mother liquor may be admixed with 4 to 6 ml of $H_2O$/100 g of filtrate or of an aqueous nitric acid of appropriate water content (where 1,8-dinitroanthraquinone has been obtained by distilling off nitric acid), or may be distilled to bewteen 70 and 80 %, preferably to 75 % of its original weight, or may be admixed with 5 to 7 ml of $H_2O$/100 g of filtrate (where 1,8-dinitroanthraquinone has been separated off by the addition of water). In this case, isolation is carried out at 20° to 40°C, preferably at room temperature, by stirring for between 1 and 24 hours, preferably for 2 to 3 hours, followed by washing with 65 to 90 %, preferably with 80 % nitric acid. Yields of from 14 to 17 % of the stoichiometric yield are obtained.

More than 90 % of the $\alpha,\alpha$-dinitroanthraquinones present in the original nitration mixture are thus obtained in 3 fractions. Residual 1,5- and 1,8-dinitroanthraquinones are present with almost all the 1,6- and 1,7-dinitroanthraquinone in the mother liquor of the 1,5-1,8-dinitroanthraquinone mixture. They can be separated off from the mother liquor with the 1,6- and 1,7-dinitroanthraquinone by continued distillation or by adding more water in such a way that almost all the 2,6- and 2,7-dinitroanthraquinones together with the hydroxy dinitroanthraquinones remain in solution in the filtrate.

To this end, the previously separated fractions, where they have been isolated by the partial distillation of nitric acid, are distilled to between 55 and 65 %, preferably to 60 %. Alternatively, where they have been isolated by the addition of water, 13 to 15 ml of water are added per 100 g of filtrate. The mixture is stirred for 1 to 3 hours on completion of distillation or after the water has been added and the precipitate is separated off at 20° to 40°C, preferably at 25° to 30°C. This gives a yield of 15 to 20 % of the theoretical of a mixture of which about 70 to 75 % consists of 1,6- and 1,7-dinitroanthraquinone (in substantially equal proportions) and which contains 18 to 25 % of 1,8-dinitroanthraquinone and 1 to 4 % of 1,5-dinitroanthraquinone. 2,6- and 2,7-dinitroanthraquinone and the hydroxy dinitroanthraquinones remain in the residual filtrates.

On completion of fractionation, it is thus possible to obtain in fractionated form from 90 to 95 % of the $\alpha,\alpha$- and $\alpha,\beta$-dinitroanthraquinones originally present in the reaction mixture.

Where the process according to the invention is used for the production of pure 1,5-dinitroanthraquinone, purification of the crude 1,5-dinitroanthraquinone yields an extract which contains almost exclusively 1,5- and predominantly 1,8-dinitroanthraquinone, and, optionally after the 1,8-dinitroanthraquinone has been separated off, a third fraction which also consists of 1,5- and, predominantly, 1,8-dinitroanthraquinone. These mixtures may be isolated as such and used for reactions. However, the extract and/or the third fraction may be introduced into the next dinitration batch of anthraquinone before or after the reaction without modifying the separation process according to the invention in any way. In this connection, the extract and/or third fraction can be isolated or subjected to intermediate drying, although this is not absolutely essential. In cases where both the extract and the third fraction are introduced in this way, the second dinitration results in almost complete separation of the $\alpha,\alpha$-dinitroanthraquinones into pure 1,5- and pure 1,8-dinitroanthraquinone, with the exception only of those fractions which are separated off with the 1,6- and 1,7-dinitroanthraquinone i.e. at most 10 to 15% of the $\alpha,\alpha$-dinitroanthraquinone present in the dinitration mixture. In this case, a mixture of 1,5- and 1,8-dinitroanthraquinone (known commercially by the name of Gloriamehl) is no longer obtained. In this way, it is possible to obtain up to 38 % of the stoichiometric yield of pure 1,5-dinitroanthraquinone and up to 32 % of pure 1,8-dinitroanthraquinone on a laboratory scale. On a commercial scale, it is possible to obtain yields of from 36 to 37 % of pure 1,5-dinitroanthraquinone and from 29 to 30 % of the stoichiometric yield of pure 1,8-dinitroanthraquinone.

Since, in this process, there is little or no increase in the total quantity of nitric acid used for dinitration of the anthraquinone, there is little or no increase in the consumption of nitric acid compared with separation into 1,5-dnitroanthraquinone containing 1,8-dinitroanthraquinone and pure 1,8-dinitroanthraquinone. This process can be carried out both during fractionation by removing the nitric acid by fractional distillation, and also by the fractional addition of water, optionally in the form of aqueous nitric acid.

It is clear that these processes (above all the last process, namely complete separation into 1,5- and 1,8-dinitroanthraquinone) can advantageously be carried out partly or completely continuously. In this case, the reaction and/or separation is carried out by a recycle process. Not only the extracts from the purificaton of 1,5-dinitroanthraquinone and/or the third fraction, but also the nitric acid distilled off during separation are returned to the reaction apparatus, optionally following partial or complete removal of the nitrous acid. The nitric acid used during nitration and any nitric acid lost during separation is replenished, for example by fresh nitric acid introduced during washing of the individual fractions or by fresh nitric acid introduced into the reaction. The water of reaction and the water additionally introduced during the washes or by the addition of water where separation is carried out by the fractional addition of water, remain in the sump of the 1,6- and 1,7-dinitroanthraquinone fraction or in the sump of the Gloriamehl fraction. The nitric acid in the sump can be recovered by distillation in the form of dilute nitric acid which can be used for washing. Alternatively it can be recovered by distillation using anhydrous $H_2SO_4$ in the form of highly concentrated nitric acid which can be delivered to the reaction circuit.

In the following Examples, the analyses are based on quantitative column chromatography of the nitroanthraquinones and of the aminoanthraquinones obtained from them by complete reduction. The relative percentage errors of the analyses are as follows: $\pm 0.5$ % at values above 50 %; $\pm 5$ % at values of from 1 to 10 %; $\pm 1$ % at values of from 10 to 50 %; $\pm 10$ % at values below 1 %.

The $HNO_3$-concentration figures are based on titrations. The empirically determined solids content (precipitation by heavy $H_2O$-dilution, isolation and weighing) and the analytically determined content of nitrous acid were deducted beforehand. Owing to smaller $HNO_3$-losses during the reaction and to the additional consumption of $HNO_3$ by secondary reactions (for example oxidation), they are somewhat lower than the figures calculated on the basis of stoichiometry.

In the examples, temperatures are expressed in °C. In connection with the yields obtained, % of the theoretical means % of the stoichiometrically possible yield.

EXAMPLE 1 a. Preliminary reaction for obtaining an extract from crude 1,5-dinitroanthraquinone and a third fraction consisting of a mixture of 1,5- and 1,8-dinitroanthraquinone 300 g of 99 % anthraquinone are introduced over a period of 10 minutes with stirring and cooling with ice/water into 1.2 liters of 98 % nitric acid. The mixture is left to react for 3 hours at 35°C and then for 1 hour at 68 to 72°C. It is then left to cool while stirring, followed by stirring for a further 10 to 15 hours at 20° to 25°C. The precipitate formed is filtered under suction or pressed on a closed suction filter provided with a stirrer, giving approximately 250 g of filter cake I and approximately 1760 g of filtrate I.

With the suction filter closed, the filter cake I is stirred for 2 hours with 200 ml of cold 98 % $HNO_3$. Filtration under suction is followed by washing with 230 ml of 98 % HNO₃, leaving filter cake and extract 1 (= filtrate + HNO₃-wash).

The filter cake when washed until neutral and dried consists of 135 g of 1,5-dinitroanthraquinone. Quality: 98.4 %. Pure 1,8-dinitroanthraquinone is obtained as follows from filtrate I (HNO₃-concentration: 93.7 %): nitric acid is distilled of at 60° to 70°C in a partial vacuum until 75 % of the original weight is left as residue (HNO₃-concentration: 92.2%). The residue is stirred for 1 to 2 hours in the absence of heat, as a result of which the 1,8-dinitroanthraquinone precipitates in the form of coarse crystals. It is filtered under suction at 25° to 30°C and washed with 180 ml of 80 % HNO₃, leaving filter cake II and filtrate II (= original filtrate + HNO₃-wash), HNO₃-concentration: 90.3 %. The filter cake is washed until neutral and dried, giving 69.2 g of 1,8-dinitroanthraquinone, quality: 98.8 %.

A mixture of 1,5- and 1,8-dinitroanthraquinone is isolated as follows from filtrate II:

Nitric acid is distilled off at 60° to 70°C in a partial vacuum until 70 % of the original weight is left as residue (HNO₃-concentration: ≈85 %). The residue is then stirred for 2 hours in the absence of heat, and the precipitate is filtered off under suction and thoroughly pressed, leaving approximately 160 g of HNO₃-moist filter cake III and filtrate III.

b. Main reaction with addition of extract and fraction III from (a)

The filter cake III is washed away from the suction filter under suction with the necessary quantity of cold 98 % HNO₃ (approximately 600 ml). The solution thus obtained is combined with extract 1 and 98 % HNO₃ is added in such a quantity that a total volume of 1600 to 1700 ml is present (HNO₃-concentration: ≈97 %). 300 g of anthraquinone are again introduced into this solution as already described, and the mixture is left to react in the same way as described above. On completion of the reaction, the mixture is stirred cold for 10 hours (HNO₃-concentration: 93.5 – 94.5 %), filtered under suction at 25° and washed with 180 ml of 98 % HNO₃. Filter cake IV and filtrate IV are obtained (HNO₃-concentration: 93.7 – 94.8 %). The filter cake IV is treated in the same way as filter cake I, and filtrate IV in the same way as filtrate I. In the same way as before, pure 1,5-dinitroanthraquinone and extract are obtained from filter cake IV, pure 1,8-dinitroanthraquinone is obtained from filtrate IV and a moist mixture of 1,5- and 1,8-dinitroanthraquinone from its filtrate.

The extract obtained after this reaction and the solution of the HNO₃-moist mixture of 1,5-and 1,8-dinitroanthraquinone in 98 % HNO₃ are again introduced into the next batch of anthraquinone for dinitration in the same way as described above, i.e. made up with 98 % nitric acid to a volume of 1600 to 1700 ml, 300 g of anthraquinone added, the reaction carried out and the reaction mixture separated in the same way as described above.

After the reaction has been repeated five times, in each case using the extract and the third fraction (1,5- + 1,8-dinitroanthraquinone) from the preceding batch, the following overall result is obtained:

Anthraquinone input: 1500 g of 99 % anthraquinone
1,5-dinitroanthraquinone: 825 g pure yield: 37.7 %
  Analysis:
97.7 % of 1,5-dinitroanthraquinone;
1.6 % of 1,8-dinitroanthraquinone;
0.2 % of 1,6-dinitroanthraquinone;
0.1 % of 1,7-dinitroanthraquinone;
0.4 % of 1-nitroanthraquinone.

1,8-dinitroanthraquinone: 608 g pure yield: 28.3 %
  Analysis:
98.3 % of 1,8-dinitroanthraquinone;
0.6 % of 1,5-dinitroanthraquinone;
0.4 % of 1,6-dinitroanthraquinone;
0.4 % of 1,7-dinitroanthraquinone;
0.1 % of hydroxy-dinitroanthraquinone.

EXAMPLE 2

300 g of 99 % anthraquinone are introduced over a period of 10 minutes while stirring and cooling with ice into 1.2 liters of 98 % nitric acid. The mixture is left to react for 3 hours at 40° to 42°C and then for 1 hour at 68° to 72°C. The reaction mixture is left to cool while stirring, followed by stirring for a further 10 to 15 hours at 20° to 25°C. The precipitate obtained in this way is filtered under suction or thoroughly pressed on a closed suction filter equipped with a stirrer, giving approximately 250 g of filter cake and approximately 1760 g of filtrate I.

With the suction filter closed, the filter cake is stirred for 2 hours on the suction filter with 200 ml of cold 90 % HNO₃. Filtration under suction is follwed by washing with 230 ml of 98 % HNO₃, leaving a filter cake and extract 1 (=filtrate + HNO₃-wash).

The filter cake is washed until neutral and dried, and then consists of 135 g of 1,5-dinitroanthraquinone with the following composition:
98.4 % of 1,5-dinitroanthraquinone;
1.1 % of 1,8-dinitroanthraquinone;
0.1 % of 1,7-dinitroanthraquinone;
traces of 1,6-dinitroanthraquinone;
0.4 % of 1-nitroanthraquinone;
pure yield: 31.0 % of the theoretical.

Extract 1 (450 ml with a solids content of approximately 50 g ) is made up to 1.2 liters with 98 % HNO₃, and then reacted as described above with 300 g of 99 % anthraquinone. The deposit formed is filtered off under suction and washed with 180 ml of 98 % HNO₃. Approximately 320 g of filter cake and approximately 1960 g of filtrate II (= filtrate + HNO₃-wash) are obtained. With the suction filter closed, the filter cake is stirred for 2 hours with 200 ml of cold 98 % HNO₃. The mixture is subsequently filtered under suction and then washed with 230 ml of 98 % HNO₃, leaving an extracted filter cake and extract 2 (= filtrate + HNO₃-wash) of approximately 480 ml. The filter cake is washed until neutral and then dried and consists of 145 g of 1,5-dinitroanthraquinone with the following composition:
98.2 % 1,5-dinitroanthraquinone;
1.2 % of 1,8-dinitroanthraquinone;
0.1 % of 1,7-dinitroanthraquinone;
0.1 % of 1,6-dinitroanthraquinone;
0.4 % of 1-nitroanthraquinone;
pure yield: 33.5 % of the theoretical.

HNO₃ is distilled off from filtrate II (HNO₃-concentration 93.8 %) in partial vacuum at 60° to 70°C until 75 % by weight of the original weight are left as residue (HNO₃-concentration: 91.6 %). The residue is stirred cold for 2 hours, as a result of which 1,8-dinitroanthraquinone is precipitated in the form of coarse crystals. It is filtered under suction at 25° to 30°C and washed with 180 ml of 80 % HNO₃, leaving behind a filter cake and filtrate III (= filtrate + HNO₃-wash) of approximately 1630 g = 1100 ml (HNO₃-concentration 89.8 %). The filter cake when washed until neutral and dried consists of 70.2 g of 1,8-dinitroanthraquinone of the following composition:
99.2 % of 1,8-dinitroanthraquinone;
0.4 % of 1,5-dinitroanthraquinone;
0.2 % of 1,7-dinitroanthraquinone;
0.1 % of 1,6-dinitroanthraquinone;
pure yield: 16.4 % of the theoretical.

Extract 2 is used like extract 1 for the next dinitration of anthraquinone, i.e. it is made up to 1.2 liters with 98 % HNO₃ and 300 g of anthraquinone are added. The extracts are reused in the same way for all the reactions. After five repetitions, the result obtained is substantially the same as that obtained from the first run described above.

Yield: 151 g of 1,5-dinitroanthraquinone
Composition:
97.9 % of 1,5-dinitroanthraquinone;
1.4 % of 1,8-dinitroanthraquinone;
0.5 % of 1-nitroanthraquinone;
0.1 % of 1,6-dinitroanthraquinone;
0.1 % of 1,7-dinitroanthraquinone;
Yield: 72.3 g of 1,8-dinitroanthraquinone.

Composition:
98.8 % of 1,8-dinitroanthraquinone;
0.3 % of 1,5-dinitroanthraquinone;
0.5 % of 1,6-dinitroanthraquinone;
0.4 % of 1,7-dinitroanthraquinone.

Pure 1,8-dinitroanthraquinone can also be obtained from filtrate I by the procedure described in reference to filrate II.

In addition to residual 1,5-and 1,8-dinitroanthraquinone, filtrate III contains the 1,6- 1,7-, 2,6- and 2,7-dinitroanthraquinones formed during the reaction and the hydroxydinitroanthraquinones formed by oxidation, the exact constitution of which was not determined.

Filtrate III may be processed by any one of the following methods:

1. It can be stirred into excess water, and the precipitate formed filtrate off under suction, washed until neutral and finally dried. 184 g of a product of substantially the following composition are obtained in this way:
10.7 % of 1,5-dinitroanthraquinone;
38.9 % of 1,8-dinitroanthraquinone;
18.8 % of 1,6-dinitroanthraquinone;
20.5 % of 1,7-dinitroanthraquinone;
2.0 % of 2,6-dinitroanthraquinone;
1.5 % of 2,7-dinitroanthraquinone;
5.8 % of hydroxy-dinitroanthraquinone;
0.2 % of 1-nitroanthraquinone.

2. It can be freed from 2,6- and 2,7-dinitroanthraquinone and from hydroxy dinitroanthraquinone by the following method:

HNO₃ is distilled off in a partial vacuum at 60° to 70°C until 50 % of the original weight are left as residue (HNO₃-concentration: 78.3 %). After stirring for 2 hours in the absence of heat, the precipitate is filtered off under suction, washed with 150 ml of 65 % HNO₃ and then with water until it is neutral, and finally dried. 152 g of a product of the following composition are obtained in this way:
12.8 % of 1,5-dinitroanthraquinone;
43.8 % of 1,8-dinitroanthraquinone;
19.4 % of 1,6-dinitroanthraquinone;
22.2 % of 1,7-dinitroanthraquinone;
0.7 % of hydroxy-dinitroanthraquinone;
0.2 % of 1-nitroanthraquinone.

3. The mixture obtainable in accordance with method (2) can also be divided up into two fractions:
a. 1,5- and 1,8-dinitroanthraquinone free from 1,6-and 1,7-dinitroanthraquinone, and
b. 1,6- and 1,7-dinitroanthraquinone free from 2,6-and 2,7-dinitroanthraquinone, for example in accordance with the following procedure:

HNO₃ is distilled off in a partial vacuum at 60° to 70°C until 80 % (= approximately 1300 g ) of the original weight are left as residue (HNO₃-concentration 86.9 %). After stirring for 2hours in the absence of heat, the precipitate formed is filtered off under suction and washed with 180 ml of 80 % HNO₃. Fraction (a) is present in the filter cake. Fraction (b) is recovered from the filtrate (approximately 1460 g ) by distilling off HNO₃ until 65 % by weight remain in the residue (HNO₃-concentration 79 %), stirring while cold for 2 hours in the absence of heat, filtering under suction and washing with 100 ml of 65 % HNO₃.

Yield (a): 65.2 g.
Composition:
76 % of 1,8-dinitroanthraquinone;
20.6 % of 1,5-dinitroanthraquinone;
0.6 % of 1,6-dinitroanthraquinone;
1.3 % of 1,7-dinitroanthraquinone;
0.5 % of hydroxy-dinitroanthraquinone.

Yield (b): 80.5 g.
Composition:
38.1 % of 1,7-dinitroanthraquinone;
34.9 % of 1,6-dinitroanthraquinone;
19.3 % of 1,8-dinitroanthraquinone;
4.8 % of 1,5-dinitroanthraquinone;
0.3 % of 2,6-dinitroanthraquinone;
<0.3 % of 2,7-dinitroanthraquinone;
1.3 % of hydroxy-dinitroanthraquinone.

Aqueous nitric acid or nitric acid with a minimum content of 95 % is redistilled from the filtrates left following separation of the 1,6- and 1,7-dinitroanthraquinone, either by direct distillation or by distillation after the addition of anhydrous sulphuric acid.

The residue contains almost all the 2,6- and 2,7-dinitroanthraquinone formed during the reaction and several hydroxy dinitroanthraquinones in addition to residual 1,5-, 1,6-, 1,7- and 1,8-dinitroanthraquinones.

EXAMPLE 3 a. The procedure is as described in Example 2, except that 1.5 liters instead of 1.2 liters of 98 % HNO₃ are used, and the mixture left to react for 20 hours at 20° to 25°C. 200 ml of HNO₃ are then distilled off in a partial vacuum at 60° to 70°c, and the distillation residue is stirred cold for several hours. Working up (extraction, separation etc.) is carried out in the same way as in Example 2.

Before being reused for the next reaction, the extracts are always made up to 1.5 liters with 98 % nitric acid. The result obtained is similar to the result obtained in Example 2.

b. The procedure is as described in Example 3(a), except that 120 ml of anhydrous sulphuric acid are added before the nitric acid is distilled off.

c. The procedure is as described in Example 3(a), except that 120 ml of anhydrous sulphuric acid are added after the nitric acid has been distilled off, followed by stirring in the absence of heat.

EXAMPLE 4 a. The procedure is as described in Example 2, except that the nitric acid is recycled. To this end, the extract and the wash (approximately 480 ml) of the 1,5-dinitroanthraquinone precipitate are made up with the nitric acid distilled off (approximately 550 ml) before isolation of the second (1,8-) and third (1,5- and 1,8-dinitroanthraquinone)-fractions, and with some of the nitric acid distilled off (approximately 340 ml) before isolation of the fourth (1,6- and 1,7-dinitroanthraquinone)-fraction from the predeeding reaction, and 300 g of anthraquinone are allowed to react therein in the same way as described above. Fractionation is then carried out in the same way as in Example 2.

Following separation of the 1,6- and 1,7-dinitroanthraquinone fraction, aqueous nitric acid is recovered from the sump by dry distillation under reduced pressure, being adjusted to an $HNO_3$-content of 80 % with the remaining residue of the concentrated $HNO_3$ distillates or, optionally, even with fresh 98 % nitric acid, and used as washing acid. The losses of nitric acid caused by the reaction and by separation are adjusted by introducing the requisite quantity in the form of the 80 % washing nitric acid.

b. The procedure is as described in Example 1, except that the $HNO_3$ is recycled. To this end, fraction 3 (1,5-and 1,8-dinitroanthraquinone mixture) from the preceding dinitration is combined with the extract left after purification of the 1,5-dinitroanthraquinone from the preceding dinitration stage, followed by further processing in the same way as described in 4(a).

EXAMPLE 5

The procedure is as described in Example 2, except that following introduction of the anthraquinone the mixture is left to react as follows:
for 3 hours at 25° to 30°C
for 1 hour at 40° to 45°C
for 1 hour at 68° to 72°C.

Filtrate II is worked up by a different procedure from that adopted in Example 2. 72 ml of water are added to it, followed by heating until a clear solution is obtained (temperature required approximately 70°C). The solution is then stirred for 2 to 3 hours, and the coarse-crystalline precipitate formed is filtered off under suction at 25° to 30°C and washed with 180 ml of 80 % $HNO_3$.

Filter cake and filtrate IV (= original filtrate + $HNO_3$-wash, $HNO_3$-concentration: 90.3 %) are obtained. The filter cake when washed until neutral and dried gives 73.2 g of 1,8-dinitroanthraquinone with the following composition:
98.6 % of 1,8-dinitroanthraquinone;
0.4 % of 1,5-dinitroanthraquinone;
0.4 % of 1,6-dinitroanthraquinone;
0.4 % of 1,7-dinitroanthraquinone;
pure yield: 17.2 % of the theoretical.

Residual 1,5- and 1,8-dinitroanthraquinone can be isolated in the form of a pure mixture from filtrate IV (approximately 2150 g) by any of the following methods:
a. $HNO_3$ is distilled off (under a partial vacuum) at 60° to 70°C until 80 % of the original weight of the filtrate are left as residue. After stirring for 2 hours in the absence of heat, the precipitate formed is filtered off under suction, washed with 180 ml of 80 % $HNO_3$, and then with water until it is neutral, followed by drying.

62.6 g of a product with the following composition are obtained:
77.1 % of 1,8-dinitroanthraquinone;
18.9 % of 1,5-dinitroanthraquinone;
0.6 % of 1,6-dinitroanthraquinone;
1.8 % of 1,7-dinitroanthraquinone;
0.8 % of hydroxy-dinitroanthraquinone.

Original filtrate + $HNO_3$-wash: approximately 1790 g. Another fraction consisting predominantly of 1,6-and 1,7-dinitroanthraquinone can be isolated therefrom in a yield of 19 to 21 % of the theoretical by distillation at 55 – 60 % ($HNO_3$-concentration: 78%).

b. 108 ml of water are added ($HNO_3$-concentration: 82 %). The product is briefly heated to 70°C and stirred for 3 hours in the absence of heat. The precipitate formed is filtered off under suction at room temperature, washed with 180 ml of 80 % $HNO_3$ and then with water until it is neutral, followed by drying. 61.1 g of a product with the following composition are obtained:
76.7 % of 1,8-dinitroanthraquinone;
19.3 % of 1,5-dinitroanthraquinone;
0.7 % of 1,6-dinitroanthraquinone;
1.7 % of 1,7-dinitroanthraquinone;
0.5 % of hydroxy-dinitroanthraquinones;

Original filtrate + $HNO_3$-wash: approximately 2300 g.

Another fraction consisting predominantly of 1,6- and 1,7-dinitroanthraquinone can be separated off therefrom in a yield of 20 to 21 % by adding another 540 ml of $H_2O$ ($HNO_3$-concentration: 67 %)

Composition:
34.6 % of 1,6-dinitroanthraquinone;
38.4 % of 1,7-dinitroanthraquinone;
20.7 % of 1,8-dinitroanthraquinone;
4.0 % of 1,5-dinitroanthraquinone;
0.5 % 2,6- and 2,7-dinitroanthraquinone;
1.1% of hydroxy-dinitroanthraquinone.

EXAMPLE 6

The procedure is as described in Example 5, except that the mixed dinitration of anthraquinone is carried out not only with the extract left after stirring of the 1,5-dinitroanthraquinone, but also with the $HNO_3$-moist filter cake containing 1,5- and 1,8-dinitroanthraquinone obtained in accordance with variant (a) or (b) of Example 5.

EXAMPLE 7

360 g of a mixture with the composition:
19.9 % of anthraquinone;
43.2 % of 1-nitroanthraquinone;
17.7 % of 2,-nitroanthraquinone;
5.5 % of 1,5-dinitroanthraquinone;
7.0 % of 1,8-dinitroanthraquinone;
1.3 % of 1,6-dinitroanthraquinone;
1.9 % of 1,7-dinitroanthraquinone;
0.5 % of 2,6- and 2,7-dinitroanthraquinone;
2.7 . of hydroxy-dinitroanthraquinone;
are obtained from the mother liquor left after the mononitration of anthraquinone in nitric acid by stirring into 5 times the volume of water, filtering under suction, washing until neutral and drying. The mixture is stirred in 1200 ml of 98 % $HNO_3$ for 3 hours at 35° to 40°C and for 1 hour at 70° to 75°C. A sample made into a paste with water and then worked up has the following composition:

- 0.2 % of 1-nitroanthraquinone;
- 35.9 % of 1,5-dinitroanthraquinone;
- 33.6 % of 1,8-dinitroanthraquinone;
- 12.6 % of 1,6-dinitroanthraquinone;
- 13.4 % of 1,7-dinitroanthraquinone;
- 1.1 % of 2,6-dinitroanthraquinone;
- 1.0 % of 2,7-dinitroanthraquinone;
- 2.0 % of hydroxy dinitroanthraquinone.

26 ml of water are stirred into the still warm reaction mixture which is then stirred overnight in the absence of heat, filtered under suction, washed with 100 ml of 98 % $HNO_3$ and filtered in a press. The $HNO_3$-moist filter cake is stirred for 2 hours with 200 ml of cold 98% $HNO_3$, and the residual solids are filtered off under suction and washed with 230 ml of $HNO_3$. A filter cake and extract (= liquid phase + $HNO_3$-wash) are obtained. After washing until neutral and drying, the filter cake yields 102 g. The extract is made up to 1.2 liters with 98% $HNO_3$ and reused for nitrating 360 g of dry mother liquor product with the above composition (from mononitration).

45 ml of $H_2O$ are then added, and the product is stirred overnight after cooling, filtered under suction and washed with 180 ml 98% $HNO_3$ = filtrate I and filter cake.

The filter cake is stirred for 2 hours in 200 ml of cold 98% $HNO_3$, filtered under suction, washed with 230 ml of 98% $HNO_3$ and then with water until it is neutral, followed by drying.

Yield: 123.8 g of 1,5-dinitroanthraquinone, quality: 99.0%. The filtrate = 2050 g is divided into 2 equal fractions, namely fraction A and fraction B.

Fraction A: separation by distillation in accordance with Example 2 gives :

1,8-dinitroanthraquinone 31.3 g = 14.7 %, quality: 98.2 %; 1,5- and 1,8-dinitroanthraquinone(free from 1,6- and 1,7-dinitroanthraquinone) 28.6 g = 13.4%, 1,6- and 1,7-dinitroanthraquinone)free from 2,6- and 2,7-dinitroanthraquinone) 52.7 g = 24.2%.

Fraction B: separation by the fractional addition of water in accordance with Examples 5 and 5 (b) gives:

1,8-dinitroanthraquinone: 30.2 g = 14.2%, quality: 97.9%; 1,5- and 1,8-dinitroanthraquinone (free from 1,6- and 1,7-dinitroanthraquinone): 30.4 g = 14.3% 1,6- and 1,7-dinitroanthraquinone (free from 2,6- and 2,7-dinitroanthraquinone): 50.6 g = 23.9%.

EXAMPLE 8

300 g of anthraquinone are gradually introduced over a period of 2 hours at 3° to 5°C into a mixture of 1000 ml of 98% $HNO_3$ and 110 ml of monohydrate, followed by stirring for 4 hours at the same temperature. After heating to 20°–25°C, the mixture is stirred for 1 hour at that temperature. In order to improve the absorption capacity of the deposit formed, it is stirred for another hour at 70°C, and then stirred in the absence of heat, filtered under suction, washed with 180 ml of 98% $HNO_3$ and filtered in a press. A filter cake and filtrate (1920 g = original filtrate + $HNO_3$ wash) are obtained. The filter cake is stirred with 200 ml of 98% $HNO_3$ in the suction filter, first for 1 hour at 65° to 70°C and then for 2 hours at room temperature filtered off under suction, and then washed with 230 ml of 98% $HNO_3$. A filter cake and extract (filtrate left after stirring and $HNO_3$ wash) are obtained. The filter cake is washed until neutral and dried. Yield: 134.2 g.

Composition:
- 98.2 % of 1,5-dinitroanthraquinone;
- 1.4 % of 1,8-dinitroanthraquinone;
- 0.1 % of 1-nitroanthraquinone;
- 0.1 % of 1,7-dinitroanthraquinone;
- traces of 1,6-dinitroanthraquinone.

The extract is made up to 1000 ml with 98% $HNO_3$ and 110 ml of monohydrated are added. The mixture is reacted as described above with 300 g of anthraquinone, and the reaction product worked up and the filter cake obtained re-extracted.

154 g of 1,5-dinitroanthraquinone of the following compositions are obtained:
- 97.6 % of 1,5-dinitroanthraquinone;
- 1,9 % of 1,8-dinitroanthraquinone;
- 0.15 % of 1-nitroanthraquinone;
- 0.1 % of 1,7-dinitroanthraquinone;
- 0.1 % of 1,6-dinitroanthraquinone;
- pure yield: 35.2 % of the theoretical.

Nitric acid is distilled off from the extract (1890 g) under a partial vacuum at 60° to 70°C until 980 g are left as residue. The product is stirred cold at 40° to 45°C, filtered under suction in a slightly preheated suction filter, and washed with 220 ml of 80 % $HNO_3$ at 40°C. The filter cake when washed until neutral and dried gives 178 g or 41.7% of the theoretical amount of 1,8-dinitroanthraquinone with the following composition:
- 85.7 % of 1,8-dinitroanthraquinone;
- 12.2 % of 1,5-dinitroanthraquinone;
- 0.5 % of 1,6-dinitroanthraquinone;
- 0.7 % of 1,7-dinitroanthraquinone;
- 0.3 % of hydroxy-dinitroanthraquinone.

EXAMPLE 9 a. The procedure is as described in Example 8, except that the crude 1,5-dinitroanthraquinone is extracted and washed with the same volume of 98 % $HNO_3$ containing 10% by volume of monohydrate, instead of with pure 98 % $HNO_3$.

The extract is then made up to 1100 ml with 98% $HNO_3$ containing 10% by volume of monohydrate for the next dinitration, and reacted with 300 g of anthraquinone. The result obtained is substantially the same as that obtained in Example 8.

b. The procedure is as described in Example 8, except that the 110 ml of anhydrous sulphuric acid are replaced by 240 g of perfluorbutane sulphonic acid and the mixture is stirred for 5 hours at 5 to 10°C and then for 15 hours at room temperature. A sample made into a paste has the following composition:
- 42.2 % of 1,5-dinitroanthraquinone;
- 40.6 % of 1,8-dinitroanthraquinone;
- 6.3 % of 1,6-dinitroanthraquinone;
- 6.6 % of 1,7-dinitroanthraquinone;
- 0.5 % of 2,6-dinitroanthraquinone;
- 0.4 % of 2,7-dinitroanthraquinone;
- 1.0 % of 1-nitroanthraquinone;
- 1.2 % of hydroxy-dinitroanthraquinone.

The reaction mixture is separated in the same way as described in Example 8. The perfluorbutane sulphonic acid remains in the sump product left after separation.

EXAMPLE 10

150 g of anthraquinone are uniformly stirred quickly over a period of 2 hours at 5° to 8°C into a mixture of 600 ml of 98 % $HNO_3$ and 70 ml of anhydrous sulphuric acid. After stirring for another 2 hours at 5° to 10°C, the mixture is heated to 70°C and kept at that temperature for 1 hour. It is then cooled while stirring in a water bath to 30°C, stirred for 1 hour at that temperature, filtered under suction and washed with 45 ml of 98 % $HNO_3$.

Filter cake I and filtrate I (= original filtrate + $HNO_3$-wash) = 1017 g are obtained. The filter cake I is washed until neutral and dried. Yield: 97.7 g. The filter cake is stirred for 2 hours at room temperature in 125 ml of 98 % $HNO_3$, and the undissolved components are filtered off under suction and washed with 115 ml of 98 % $HNO_3$. Filter cake and extract I (liquid phase left after stirring + $HNO_3$ wash = 220 ml) are obtained. The filter cake is washed until neutral and dried, giving 68.8 g of 97.9 % pure 1,5-dinitroanthraquinone.

Pure 1,8-dinitroanthraquinone is isolated as follows from filtrate I : $HNO_3$ is distilled off under a partial vacuum at 60° to 70°C until 75% of the weight of the filtrate are left as residue. After stirring for 75 minutes the precipitate formed is filtered off under suction at 28°C and washed with 90 ml of 80% $HNO_3$. Filter cake II and filtrate II (=original filtrate + $HNO_3$ wash = 808 g) are obtained. The filter cake when washed until neutral and dried gives 36.6 g of 98.3 % pure 1,8-dinitroanthraquinone. A mixture of 1,5- and 1,8-dinitroanthraquinone is isolated as follows from filtrate II:

$HNO_3$ is distilled off under a partial vacuum until 75% by weight of the filtrate are left as residue. After stirring for 2 hours, the product is filtered off under suction at 25°C and then squeezed off. Filtrate III and $HNO_3$-moist filter cake III are obtained.

Extract I and $HNO_3$-moist filter cake III are made up to 700 ml and 98% $HNO_3$, followed by the addition with cooling of 80 ml of anhydrous sulphuric acid. 150 g of anthraquinone are stirred into this solution over a period of 2 hours at 5° to 10°C. The mixture is stirred for 2 hours at that temperature, subsequently heated for 1 hour to 70°C, and then stirred cold at 30°C. The precipitate is filtered off under suction and then washed with 90 ml of 98% $HNO_3$. Residue and filtrate IV (1240 g) are obtained. Filtrate IV is then processed in the same way as filtrate I, and the residue is extracted as described above giving, as already described, pure 1,5-dinitroanthraquinone and extract together with pure 1,8-dinitroanthraquinone, the filtrate of which yields a mixture of 1,5- and 1,8-dinitroanthraquinone ($HNO_3$-moist). The extract obtained and the $HNO_3$-moist filter cake, consisting of 1,5- and 1,8-dinitroanthraquinone, are reused for the next dinitration of anthraquinone, i.e. made up to 700 ml with 98% $HNO_3$, 80 ml of monohydrate added, 150 g of anthraquinone stirred in, the mixture reacted as described above and subsequently separated. After four reactions using the extract and the $HNO_3$-moist 3rd fraction (1,5- + 1,8-dinitroanthraquinone) from the preceding reaction, the following result is obtained:

Anthraquinone input: 600 g, Quality: 99%, 1,5-dinitroanthraquinone: 323 g, Pure yield: 37.2% of the theoretical.
Analysis:
97.9 % of 1,5-dinitroanthraquinone;
1.5 % of 1,8-dinitroanthraquinone;
0.2 % of 1,6-dinitroanthraquinone;
0.1 % of 1,7-dinitroanthraquinone;
0.2% of 1-nitroanthraquinone.

1,8-dinitroanthraquinone: 259 g; Pure yield: 29.9 % of the theoretical.
Analysis:
98.3 % of 1,8-dinitroanthraquinone;
0.5 % of 1,5-dinitroanthraquinone;
0.5 % of 1,6-dinitroanthraquinone;
0.4 % of 1,7-dinitroanthraquinone;
0.2 % of hydroxy-dinitroanthraquinone.

EXAMPLE 11

150 g of anthraquinone are uniformly introduced quickly over a period of 3 hours at 0° to 5°C into a mixture of 600 ml of 98% $HNO_3$ and 69 ml of anhydrous sulphuric acid. After stirring for a further 2 hours at 5° to 10°C, the mixture is heated to 70°C and kept at that temperature for 30 minutes. It is then cooled while stirring in a water bath to 25°C, stirred at that temperature for 30 minutes to 1 hour, filtered under suction and washed with 45 ml of 98% $HNO_3$.

Filter cake and filtrate I (= original wash) = + $HNO_3$ -1018 g are obtained. The filter cake is washed until neutral and dried. Yield: 97.7 g. The filter cake is stirred for 2 hours at room temperature in 125 ml of 98. $HNO_3$, filtered under suction and washed with 115 ml of 98% $HNO_3$. A filter cake and extract (= liquid phase left after stirring + $HNO_3$-wash = 220 ml) are obtained. The filter cake is washed until neutral and dried, giving 68.8 g of 1,5-dinitroanthraquinone of the following composition:

97.9 % of 1,5-dinitroanthraquinone;
1.5 % of 1,8-dinitroanthraquinone;
0.2 % of 1,6-dinitroanthraquinone;
0.1 % of 1,7-dinitroanthraquinone;
0.2 % of 1-nitroanthraquinone.

Filtrate I = 1018 g is divided into 2 fractions each weighing 509 g (fractions A and B).

Fraction A $HNO_3$ is distilled off from this fraction under a partial vacuum at 60° to 70°C until 370 g are left as residue, followed by stirring for 75 minutes after which the precipitate formed is filtered under suction at 28°C and washed with 45 ml of 80% $HNO_3$. Filter cake and filtrate II (= original filtrate + $HNO_3$ wash) are obtained. The filter cake is washed until neutral and dried, giving 18.3 g of 1,8-dinitroanthraquinone with the following composition:

98.3 % of 1,8-dinitroanthraquinone;
0.5 % of 1,5-dinitroanthraquinone;
0.5 % of 1,6-dinitroanthraquinone;
0.4 % of 1,7-dinitroanthraquinone;

$HNO_3$ is distilled off from filtrate II (404 g) until 300 g are left as residue. After stirring for 2 hours, the mixture is filtered under suction at 25° to 30°C and washed with 30 ml of 80% $HNO_3$.

Filter cake and filtrate III (= original filtrate + $HNO_3$-wash) are obtained. The filter cake is washed until neutral and dried, producing 17.1 g of a mixture of 1,5- and 1,8-dinitroanthraquinone which contains no more than 4% of other compounds.

Filtrate III (355 g) is distilled down to 195 g under a partial vacuum, and the distillation residue is stirred cold for 2 hours, filtered under suction and washed with 25 ml of 65% $HNO_3$, giving 18.4 g of a mixture of 1,6- and 1,7-dinitroanthraquinone which contains 15 to 20% of 1,8-dinitroanthraquinone but which is free from 2,6- and 2,7-dinitroanthraquinone.

Fraction B 22 ml of water are added to this fraction, followed by heating until a clear solution is formed. The product is then stirred for 2 hours in the absence of heat. The 1,8-dinitroanthraquinone precipitated is filtered under suction at 28° to 30°C and washed with 45 ml of 80% $HNO_3$. Filter cake and filtrate IV (= original filtrate + $HNO_3$-wash) are obtained. The filter cake is washed until neutral and dried, giving 19.9 g of 1,8-dinitroanthraquinone with the composition:

98.4 % of 1,8-dinitroanthraquinone;
0.5 % of 1,5-dinitroanthraquinone;
0.2 % of 1,6-dinitroanthraquinone;
0.5 % of 1,7-dnitroanthraquinone.

28 ml of water are added with stirring over a period of 15 minutes at 60° to 70°C to filtrate IV (555 g). The product is stirred for 3 hours, filtered under suction at 25°C and then washed with 45 ml of 80% $HNO_3$. Filter cake and filtrate V (= original filtrate + $HNO_3$-wash) are obtained. The filter cake is washed until neutral and dried, giving 15.3 g of a mixture of 1,5- and 1,8-dinitroanthraquinone in a ratio of about 1:4. The mixture contains no more than 3%, of other impurities.

105 ml of water are added at 60 to 70°C to filtrate V (606 g). The mixture is stirred cold for 2 hours, filtered under suction and washed with 25 ml of 65% $HNO_3$. Washing until neutral and drying leaves 14 g of 1.6- and 1,7-dinitroanthraquinone each containing 0.1 to 0.2 % of 2,6- and 2,7-dinitroanthraquinone, whilst more than 90% of the $\beta,\beta$-dinitroanthraquinones formed during nitration remain in the filtrate.

EXAMPLE 12

80 ml of anhydrous $H_2SO_4$ are introduced into a mixture of 220 ml of the extract from Example 11 and 380 ml of highly concentrated $HNO_3$ (distillates of batches fractionated in the same way as in Example 11, fraction A), density 1.51, followed by the introduction in portions with stirring over a period of 3 hours at 0° to 5°C of a total of 150 g of anthraquinone. After stirring for two hours at 5° to 10°C, the mixture is heated to 70°–72°C, kept at that temperature for 30 minutes, cooled with water to 25°C, and stirred at that temperature for 30 minutes to 1 hour. The precipitate is filtered off under suction, washed with 90 ml of 98 % $HNO_3$ and squeezed off.

Filter cake and filtrate 1 (= original filtrate + $HNO_3$-wash) are obtained. The still $HNO_3$-moist filter cake (containing approximately 105 g of solids) is stirred for 1 hour at 70°C in 125 ml of 98% $HNO_3$ and then stirred for 5 hours at room temperature. The product is separated by filtration under suction into a solid phase and a liquid phase, the solid phase being washed with 125 ml of 98% $HNO_3$. A filter cake and extract (= liquid left after stirring + $HNO_3$ wash) are obtained. The filter cake when washed until neutral and then dried yields 80.1 g of 1,5-dinitroanthraquinone with the following composition:

98.0 % of 1,5-dinitroanthraquinone;
1.5 % of 1,8-dinitroanthraquinone;
0.3 % of 1-nitroanthraquinone;
traces of hydroxy-dinitroanthraquinone and 1,7-dinitroanthraquinone.

Pure yield: 37% of the theoretical.

Filtrate 1 = 1072 g is divided into 2 fractions each weighing 536 g (fractions A and B).

Fraction A $HNO_3$ is distilled off from this fraction at 60° to 70°C until 75% by weight (~ 400 g) are left as distillation residue. The residue is then stirred for 1.5 hours, the precipitate formed is filtered under suction at 27°C and the filter cake is washed with 45 ml of 80% $HNO_3$, leaving filter cake and filtrate 2 (= original filtrate + $HNO_3$ wash). After washing until neutral and drying the filter cake gives 24.4 g of 1,8-dinitroanthraquinone of the following composition:

99.2 % of 1,8-dinitroanthraquinone;
0.3 % of 1,5-dinitroanthraquinone;
0.1 % of 1,7-dinitroanthraquinone.
less than 0.1% of hydroxy-dinitroanthraquinone.

Pure yield: 22.8% of the theoretical.

Like filtrate 1, filtrate 2 = 428 g is distilled down to 75% and the residue is stirred for 2 hours. The precipitate formed is filtered under suction at room temperature and washed with 45 ml of 80% $HNO_3$. Filter cake and filtrate 3 are obtained. The filter cake is washed until neutral and dried, and gives 17.7 g of a product with the following composition:

21.3 % of 1,5-dinitroanthraquinone;
75.8 % of 1,8-dinitroanthraquinone;
1.0 % of 1,6-dinitroanthraquinone;
1.6 % of 1,7-dinitroanthraquinone;
0.4 % of hydroxy-dinitroanthraquine.

$HNO_3$ is distilled off from the filtrate 3 (351 g) under a partial vacuum at 60° to 70°C until 193 g are left as residue. Distillate yield: 156 g. After stirring for 2 hours, the mixture is filtered under suction at room temperature and washed with 25 ml of 65% $HNO_3$. Filter cake and filtrate 4 are obtained.

The filtrate cake when washed until neutral and dried gives 15.3 g of 1,6- and 1,7-dinitroanthraquinones which, although containing 15 to 20% of 1,8-dinitroanthraquinone, contain less than 1% of 2,6- and 2,7-dinitroanthraquinone.

Filtrate 4 is stirred into excess water, filtered under suction, washed until neutral and dried. Yield 4.4 g.

Fraction B

Fraction B has 21 ml of water added to it, followed by heating until a clear solution is obtained. After stirring for 3 hours, the thoroughly crystallised precipitate formed is filtered under suction at 26°C, and the filter cake is washed with 45 ml of 80% $HNO_3$. Original filtrate + $HNO_3$-wash = filtrate 1.

The filter cake when washed until neutral and dried consists of 25.1 g of 1,8-dinitroanthraquinone with the following composition:

99.2 % of 1,8-dinitroanthraquinone;
0.4 % of 1,5-dinitroanthraquinone;
0.1 % of 1,7-dinitroanthraquinone;
less than 0.1 % of hydroxy-dinitroanthraquinone.

30 ml of water are added at 60°C to filtrate 1(585 g), following by stirring for 2 hours. The precipitate is filtered under suction at 26°C and washed with 45 ml of 80% $HNO_3$ (filtrate 2).

The filter cake is washed with water until neutral and dried. 15.3 g of a product with the following composition are obtained:

24.3 % of 1,5-dinitroanthraquinone;
72.2 % of 1,8-dinitroanthraquinone;
0.9 % of 1,6-dinitroanthraquinone;
1.7 % of 1,7-dinitroanthraquinone.

120 ml of water are added to filtrate 2(633g) at 60° to 70°C, followed by stirring for 2 hours in the absence of heat. The precipitate formed is filtered off and washed with 30 ml of 65% HNO₃. The filter cake (18.6 g) when washed until neutral and dried consists predominantly of 1,6- and 1,7-dinitroanthraquinone, in addition to 1,2-dinitroanthraquinone, and is free from 2,6- and 2,7-dinitroanthraquinone.

The extract obtained in this Example can be reused as described above for the next dinitration of anthraquinone.

EXAMPLE 13 a. 40 g of a ground dinitroanthraquinone mixture with the following composition:
  68.8 % of 1,8-dinitroanthraquinone;
  11.9 % of 1,5-dinitroanthraquinone;
  8.5 % of 1,7-dinitroanthraquinone;
  2.8 % of 1,6-dinitroanthraquinone;
  1.0 % of 1-nitroanthraquinone;
are stirred for 1 hour at 60°C in 120 ml of 93% HNO₃. The solution is clarified, leaving a residue of 0.8 g. 5 ml of water are added to the solution which is then heated to 75°C, and then stirred cold at 30°C. The precipitate formed is filtered under suction, washed until neutral and dried. g of 98.3% pure 1,8-dinitroanthraquinone are obtained.

b. The separation described in (a) above is repeated with the difference that the solution is not clarified. The yield of 97.4 % pure product is 17.3 g.

EXAMPLE 14 a. 40 g of a dinitroanthraquinone mixture with the following composition:
  40.8 % of 1,5-dinitroanthraquinone;
  38.5 % of 1,8-dinitroanthraquinone;
  7.3 % of 1,6-dinitroanthraquinone;
  7.9 % of 1,7-dinitroanthraquinone;
  0.9 % of 1-nitroanthraquinone;
  0.6 % of 2,6-dinitroanthraquinone;
  0.7 % of 2,7-dinitroanthraquinone;
  2.2 % of hydroxy-dinitroanthraquinone;
are stirred for 2 hours in 120 ml of cold 93% HNO₃. After filtration under suction, the product is washed with 10 ml of 93% HNO₃, giving filter cake and filtrate 1 (= original filtrate + wash).

The filter cake is washed until neutral and dried, giving 16.8 g of 92.2% pure 1,5-dinitroanthraquinone.

HNO₃ is distilled off from filtrate 1 (203 g) at 60° to 70°C until 150 g are left as distillation residue. After stirring for 1.5 hours, the mixture is filtered under suction at 25° to 30°C and washed with 15 ml of 80% HNO₃. Filter cake and filtrate 2 are obtained. The filter cake when washed until neutral and dried gives 9.2 g of 98.1 % pure 1,8-dinitroanthraquinone.

Like filtrate 1, filtrate 2 (156 g) is distilled down to 117g, stirred for 2 hours, filtered under suction at 25°C and washed with 15 ml of 98% HNO₃.

6.9 g of a mixture of the following composition are obtained:
  76 % of 1,8-dinitroanthraquinone;
  20.6 % of 1,5-dinitroanthraquinone;
  0.6 % of 1,6-dinitroanthraquinone;
  1,3 % of 1,7-dinitroanthraquinone;
  0.5 % of hydroxy dinitroanthraquinone.

These 6.9 g are stirred with the 16.8 g of the crude 1,5-dinitroanthraquinone isolated as described above in 25 ml of 98% HNO₃, first for 1 hour at 70°C and then for 3 hours at 30°C. The mixture is filtered under suction, washed with 25 ml of 98% HNO₃, washed until neutral and then dried, leaving 14.2 g of 97.7 % pure 1,5-dinitroanthraquinone.

b. 40 g of the same dinitroanthraquinone mixture as used in (a) above are stirred in 80 ml of 93% HNO₃ for 30 minutes at 60°C, stirred cold for several hours, filtered under suction and washed with 20 ml of 93% HNO₃. The filter cake contains 20.4 g of dry substance. 1,5-content: 73.2 %.

5 ml of water is added to the filtrate (153 g). Heating to 70°C produces a clear solution from which 5.1 g of pure 1,8-dinitroanthraquinone are precipitated after stirring for 5 hours.
Purity: 98.9 %.

c. The product used in (a) and (b) above was obtained by stirring anthraquinone in 6 times the quantity by weight of 98% HNO₃ for 4 hours at 35° to 40°C and for 1 hour at 70°C, followed by precipitation by stirring the reaction mixture into 7 times the quantity of water. Crude yield: 98.9% of the theoretical.

EXAMPLE 15 a. 120 g of a dinitroanthraquinone mixture of the following composition:
  54.9 % of 1,5-dinitroanthraquinone;
  39.5 % of 1,8-dinitroanthraquinone;
  0.3 % of 1,6-dinitroanthraquinone;
  2.3 % of 1,7-dinitroanthraquinone;
  1.4 % of 1-nitroanthraquinone;
  0.3 % of hydroxy dinitroanthraquinone;
are stirred for 30 minutes at 75°C in 360 ml of 93 % HNO₃, followed by stirring for another 10 hours in the absence of heat.

After filtration under suction, the filter cake is washed with 30 ml of 91% HNO₃. The filter cake contains 69.7 g of solids.

HNO₃ is distilled off from the original filtrate and from the wash (556 g) at 60° to 70°C until 415 g of distillation residue are left. After stirring for 1.5 hours in the absence of heat, the 1,8-dinitroanthraquinone precipitated is filtered off at 28°C, washed with 30 ml of 90% HNO₃, washed until neutral and then dried. 28.6 g of a product with the following composition are obtained:
  98.6 % of 1,8-dinitroanthraquinone;
  0.4 % of 1,5-dinitroanthraquinone;
  0.3 % of 1,6-dinitroanthraquinone;
  0.6 % of 1,7-dinitroanthraquinone;
  0.1 % of hydroxy-dinitroanthraquinone.

b. The product used in (a) above was obtained as follows:

180 g of anthraquinone are stirred in portions over a period of 2 hours at a temperature below 40°C into a mixture of 270 ml of 98% HNO₃ and 31 ml of anhydrous sulphuric acid, followed by stirring for a further 10 hours at 40° to 45°C. After heating for 1.5 hours to 70°C, the mixture is stirred cold at 35°C, filtered under suction and washed with 200 ml of 85 % HNO₃. The filter cake is washed with water until neutral and dried. Yield: 175.5 g.

EXAMPLE 16 a. The procedure is as described in Example 15, except that a powdered product of the following composition is used:
  53.0 % of 1,5-dinitroanthraquinone;
  45.9 % of 1,8-dinitroanthraquinone;
  0.2 % of 1,6-dinitroanthraquinone;
  0.6 % of 1,7-dinitroanthraquinone;

0.3 % of 1-nitroanthraquinone;
68.2 g of a crude 89.8 % pure 1,5-dinitroanthraquinone and 28.8 g of 97.8% pure 1,8-dinitroanthraquinone are obtained.

b. The product used in (a) above was obtained as follows:

200 g of 99% anthraquinone are stirred in 800 ml of 98% $HNO_3$ for 3 hours at 40° to 42°C and then for 1 hour at 80°C. The reaction gives 1385 g of reaction mixture, 600 g of which are distilled off in vacuo at 50° to 60°C. The suspension is then stirred cold up to 40°C and then for 1 hour at 40°C. The suspension is filtered under suction at the same temperature. The filter cake is washed with 160 ml of 80% $HNO_3$ at 40°C and then with water until neutral, followed by drying. Yield: 208 g.

EXAMPLE 17

50 g batches of 1,5-dinitroanthraquinone of various origin are converted into powder form and then held under gentle reflux for 1 hour with 50 or 100 ml (cf. table) of 95 to 98% $HNO_3$ (see table), stirred cold for 3 hours, filtered under suction at 20° to 25°C, washed with 50 ml of $HNO_3$ of the same concentration as that used for extraction, subsequently washed until neutral and finally dried.

111.6 g of mother liquor product from the purification of 1-nitroanthraquinone (analysis 34.1 % of 2-nitroanthraquinone, 27.6% of 1-nitroanthraquinone, 3.4% of 1,6-dinitroanthraquinone, 3,8% of 1,7-dinitroanthraquinone, 9.3% of 1,8-dinitroanthraquinone, 1.4% of 1,5- dinitroanthraquinone and 20.4 % of anthraquinone), 67.2 g of the sump product from the distillation of 1-nitroanthraquinone (analysis 0.7% of 2-nitroanthraquinone, 0.5% of 1,6- and 1,7-dinitroanthraquinone, 14.0% of 1,5- dinitroanthraquinone, 11.0% of 1,8-dinitroanthraquinone and 69.1% of 1-nitroanthraquinone), is introduced over a period of 10 minutes at 35° to 40°C into 1750 g of 98% $HNO_3$. The mixture is heated with stirring for 3 hours to 40° to 45°C and then for 1 hour to 65° to 70°C. A sample made into a neutral paste and then dried has the following composition: 36.0% of 1,5-dinitroanthraquinone, 34.1% of 1,8-dinitroanthraquinone, 11.7% of 1,7-dinitroanthraquinone, 9.9% of 1,6-dinitroanthraquinone and 0.8% of 1-nitroanthraquinone.

The mixture is then vigorously stirred for 1 hour at room temperature and filtered under suction at room temperature. The filter cake is squeezed out, leaving 191 g of $HNO_3$-moist filter cake (solids content 146 g,

| Results: Nitration Solvent | Analysis %1,5 | Feed product %1,8 | $HNO_3$ Volume | Content | Yield g | Yield % of the theoretical | Analysis %1,5 | Final Product %1,8 |
|---|---|---|---|---|---|---|---|---|
| $HNO_3$ | 87.4 | 10.6 | 100 | 95 | 36.9 | 83.2 | 98.9 | 0.9 |
| $HNO_3$ | 82.8 | 14.1 | 100 | 98 | 34.9 | 83.1 | 98.5 | 1.1 |
| $HNO_3$ | 73.5 | 22.4 | 50 | 98 | 32.1 | 85.0 | 97.9 | 1.7 |
| $HNO_3/H_2SO_4$ | 77.2 | 18.0 | 50 | 98 | 34.0 | 87.1 | 98.8 | 1.0 |
| $H_2SO_4$ | 82.7 | 13.1 | 100 | 95 | 35.1 | 83.7 | 98.6 | 1.0 |

EXAMPLE 18

Repetition of Moiseva's method (Org. Polyprod. i. Krasitel'Moskau 1969, No. 4, 70-79).

Batches of 300 g of 99% anthraquinone are stirred for 24 hours at 24° to 25°C. with 4, 5, 6 or 7 times the quantity by volume of 98% $HNO_3$. The precipitates formed are filtered under suction, press-filtered, washed in portions with 230 ml of 98% $HNO_3$, press-filtered, washed until neutral and dried.

composition: 82.6% of 1,5-dinitroanthraquinone, 11.45% of 1,8-dinitroanthraquinone, 1.5% of 1,6-dinitroanthraquinone, 1.85% of 1,7-dinitroanthraquinone and 0.8% of 1-nitroanthraquinone) and 1802 g of filtrate I. The moist filter cake is stirred with 290 g of 98% $HNO_3$ for 1 hour at 65° to 70°C and then for 2 hours at room temperature, filtered under suction and washed in portions with 250 g of 98% $HNO_3$. 126 g of moist filter cake and 560 g of extract are obtained. The filter cake is washed until neutral and dried. Yield: 112 g,

| Results: A'none /Vol. 10 g $HNO_3$ | Yield g | 1,5-content % | 1,8-content % | 1-nitroanthraquinone % content | % error to 100 % | Yield: g 100% | % of the theoretical |
|---|---|---|---|---|---|---|---|
| 1:4 | 157.8 | 90.5 | 6.4 | 2.1 | 1.0 | 142.8 | 33.5 |
| 1:5 | 139.2 | 92.0 | 5.3 | 1.1 | 1.6 | 128.1 | 30.4 |
| 1:6 | 122.4 | 93.0 | 5.0 | 0.3 | 1.7 | 113.8 | 26.7 |
| 1:7 | 108.9 | 93.7 | 4.7 | 0.2 | 1.4 | 102.1 | 23.8 |

Accordingly, it is not possible to obtain pure 1,5-dinitroanthraquinone under the conditions quoted by Moiseva (he does not say anything about the quantity of $HNO_3$), even in cases where dilution is so heavy that the yield falls far below the 30% quoted.

EXAMPLE 19

A. A mixture of the following composition:
144.5 g of 99% anthraquinone, 1,5-dinitroanthraquinone content: 97.5%.

Nitric acid is distilled off from filtrate I under reduced pressure at 60 to 75°C until 70% by weight are left as residue. After stirring for 2 hours, the product is filtered under suction 25°C and the residue is washed with 180 ml of 80% $HNO_3$, giving 77 g of $HNO_3$-moist filter cake II and 1420 g of filtrate II. 68.1 g of 1,8-dinitroanthraquinone (98.2 % pure) are obtained from filter cake II after it has been washed neutral and dried.

Nitric acid is then distilled off from filtrate II until 82% by weight are left as residue. After stirring for 2 hours, the product is filtered under suction at 25°C and washed with 180 ml of 80% $HNO_3$, giving 53.2 g of $HNO_3$-moist filter cake III and 1315 g of filtrate III.

After washing until neutral, followed by drying, the moist filter cake III gives 46.6 g of an α,α-dinitroanthraquinone mixture (composition 24.7% of 1,5-dinitroanthraquinone, 69.6% of 1,8-dinitroanthraquinone and 3,7% of 1,6- and 1,7-dinitroanthraquinone).

Filtrate III is freed from the $HNO_3$ using an 80°C bath in a partial vacuum at 50° to 60°C. A residue of 144 g is obtained.

B. 820 ml of 98% $HNO_3$ and 323.3 g of the mixture of anthraquinone, mother liquor and sump product mentioned in (A) are added to the 560 g of extract obtained in (A), and the mixture is reacted and separated in the same way as described in (A).

A crude $HNO_3$-moist 1,5-dinitroanthraquinone is obtained (solids content 171 g, 1,5-dinitroanthraquinone content: 81.6%; 1,8-dinitroanthraquinone content: 13.1%) giving 123.3 g of pure 1,5-dinitroanthraquinone (content 97.1%) and an extract; also 83.4 g of 1,8-dinitroanthraquinone (content: 98.6%), 44.4 g of α,α-dinitroanthraquinone (1,5- and 1,8-dinitroanthraquinone content: 94.7%) and 143 g of dry sump product.

C. The extract from (B) is used as described in (B) for the nitration of a fresh mixture of anthraquinone, mother liquor and sump product. The result obtained after separation in accordance with (A) is substantially the same as in (B). Even in the event of successive repetition using an extract from the preceding purification of 1,5-dinitroanthraquinone, it is found that there is no further change in the results of separation (slight fluctuations in both directions around the yields and qualities obtained in (B).

EXAMPLE 20

A. The procedure is as described in Example 19(A), except that 75 g of 70% $HNO_3$ are added after completion of dinitration (final $HNO_3$ content 94.5%) and the product is distilled down to only 72% instead of 70% before the 1,8-dinitroanthraquinone is isolated. 226 g of moist filter cake (154 g solids content: composition 80.3 % of 1,5-dinitroanthraquinone, 12.5 % of 1,8-dinitroanthraquinone and 3.9% of 1,6- and 1,7-dinitroanthraquinone), 113 g of 1,5-dinitroanthraquinone (97.4%), 69.5 g of 1,8-dinitroanthraquinone (98.3%) and 42.4 g of α,α-dinitroanthraquinone (1,5- and 1,8-dinitroanthraquinone content 95.1%) are obtained.

B. The procedure is as described in Example 20(A), except that 21 ml of water are used instead of 75 g of 70% $HNO_3$. The result of separation is similar to that obtained in (A).

EXAMPLE 21

Nitration is carried out in the same way as described in Example 19, except that 3100 g instead of 1750 g of 98% $HNO_3$ are used.

On completion of the reaction, the mixture is cooled to 30°C over a period of 20 minutes, and diluted while stirring with 655 g of 70% $HNO_3$. The theoretical $HNO_3$ concentration is 92% (found 91.6%). After stirring for 15 hours at room temperature, the precipitate is filtered under suction, giving 190 to 195 g of $HNO_3$-moist filter cake I (solids content approximately 145 to 150g) and filtrate I (3730 to 3740 g). 1.5 times the quantity by weight of 98% $HNO_3$ is added to the $HNO_3$-moist filter cake I, followed by stirring for 1 hour at 65° to 70°C and for 2 hours at room temperature. After filtration under suction, the residue is washed in portions with 1.3 times the quaantity by weight of 98% $HNO_3$ (based on the moist filter cake used), giving 140 to 145 g of $HNO_3$-moist filter cake II and 560 to 570 g of extract I (including wash). Filter cake II washed until neutral and dried gives 104 to 106 g of 1,5-dinitroanthraquinone. Purity: 97.3%.

Extract I is made up to 3190 to 3200 g with 2630 g of 98 to 99% $HNO_3$ and reacted as described in Example 10 with
144.5 g of 99% anthraquinone;
111.6 g of mother liquor product (quality as in Example 19(A)).
67.2 g of sump product (quality as in Example 19(A)). The product is again diluted with 655 g of 70% nitric acid and isolated as described above in this Example. Filter cake I, filter cake II, extract and filtrate I are as follows: Filter cake I $HNO_3$-moist: 220 to 225 g (solids content approximately 170 to 175 g). Filter cake II $HNO_3$-moist: 137 to 139 g; solids: 114 to 116 g. Quality 97 to 97.5%
Extract I = 690 to 710 g Approximately 99% $HNO_3$ is distilled off from filtrate I = 3900 g (50 g loss of $HNO_3$ during reaction and filtration under suction) under a partial vacuum at 60° to 70°C until 76% (2960 g) are left as residue. The residue is stirred cold for 2 hours, and the precipitate formed is filtered under suction and washed with 180 ml of 80% $HNO_3$. Washing until neutral and drying leaves 73.6 g of 1,8-dinitroanthraquinone. Quality 98.4 %.

98% $HNO_3$ is added to the extract obtained after purification of the 1,5-dinitroanthraquinone in the preceding reaction in such a quantity that a total of 3200 g are obtained, and reacted with 328 g of mixture to be nitrated of the above composition, followed by separation as described above. It is found that constant results are obtained after the third re-use of extract, namely
116 to 118 g of ≥ 97% 1,5-dinitroanthraquinone;
76 to 78 g of ≥ 98 % 1,8-dinitroanthraquinone.

EXAMPLE 22

A. 300 g of 99% anthraquinone are introduced over a period of 15 minutes into 1.2 liters of 98% $HNO_3$ in such a way that a temperature of 40°C is not exceeded. This is followed by stirring for 3 hours at 40° to 42°C and for 1 hour at 65° to 70°C. 3110 g of a reaction mixture with an $HNO_3$ content of 94.4% and a solids content of 20.3% are obtained. A sample made into a paste has the following composition:
39.3 % of 1,5-dinitroanthraquinone;
36.4 % of 1,8-dinitroanthraquinone;
7.6 % of 1,6-dinitroanthraquinone;
8.1 % of 1,7-dinitroanthraquinone;
0.5 % of 2,6-dinitroanthraquinone;
0.5 % of 2,7-dinitroanthraquinone;
0.8 % of 1-nitroanthraquinone;
2.5 % of hydroxy dinitroanthraquinone;
Moist filter cake I and filtrate I are obtained after filtration under suction and pressing.

The moist filter cake I is stirred with 300 ml of 98% $HNO_3$ for 1 hour at 65° to 70°C, stirred cold for 2 hours, filtered under suction and washed with 225 ml of 98% $HNO_3$, giving moist filter cake and extract.

The filter cake washed until neutral and dried gives 129.4 g of 1,5-dinitroanthraquinone (content 97.6%).

HNO₃ is distilled off from filtrate I at 60° to 70°C until 75% by weight are left as residue. After stirring for 2 hours, the product is filtered under suction at 26°C and washed with 180 ml of 80% HNO₃, giving HNO₃-moist filter cake II and filtrate II (1225 g). After washing until neutral and drying, filter cake II gives 65 g of 1,8-dinitroanthraquinone (content 99.1%).

Filtrate II is combined with the above extract (≥ 2370 g) and nitric acid is distilled off until 65% by weight are left as residue. After stirring cold for 2 hours, the product is filtered under suction at 25°C, and washed with 180 ml of 80% HNO₃. Filter cake III and filtrate III (1660 g) are obtained.

After washing until neutral and drying, filter cake III consists of 89 g of α-dinitroanthraquinone (1,5- and 1,8-dinitroanthraquinone content 96.1%). Filtrate III is distilled to dryness in a partial vacuum at 60°C, leaving 136.2 g (analysis: 1,5-dinitroanthraquinone: 6.0%; 1,8-dinitroanthraquinone: 21.0%, 1,6-dinitroanthraquinone 22.8%; 1,7-dinitroanthraquinone 23.4%).

Extraction with hot, 5% hydrochloric acid leaves 117.5 g.

B. The procedure is as described in (A), except that filtrate I and extract are combined with one another. Pure 1,8-dinitroanthraquinone can no longer be isolated therefrom, although distillation down to 50%, followed by filtration under suction at 20° to 25°C, gives 152 g of a mixture of 1,5- and 1,8-dinitroanthraquinone containing less than 4% of impurities.

EXAMPLE 23

The procedure is as described in Example 22(A) except that the HNO₃ used was obtained by distillation from nitration mixtures before the isolation of 1,8-dinitroanthraquinone and α,α-dinitroanthraquinone mixtures (99.3% and less than 0.4% of HNO₂). The isolation of 1,8-dinitroanthraquinone is preceded by distillation down to 72%, whilst the isolation of the α,α-dinitroanthraquinone mixture is preceded by distillation down to 60%. 70 g of 99% 1,8-dinitroanthraquinone and 98 g of an α,α-dinitroanthraquinone mixture consisting of 32.8% of 1,5-dinitroanthraquinone, 64.4% of 1,8-dinitroanthraquinone, 0.9% of 1,6-dinitroanthraquinone and 2,7% of 1,7-dinitroanthraquinone, are obtained.

What is claimed is:

1. Process for recovering substantially pure 1,5- and/or 1,8-dinitroanthraquinone from dinitration mixtures optionally containing sulphuric acid or a perfluoralkane sulphonic acid which comprises
   i. adjusting the nitric acid concentration in the nitration mixture to a value of 91 to 96% for a ratio by weight of nitric acid to solids of from 2.5 : 1 to 10 : 1;
   ii. separating off the insoluble crude 1,5-dinitroanthraquinone at 15° to 50°C;
   iii. taking up the 1,5-dinitroanthraquinone with 90 to 100% nitric acid in a ratio by weight of nitric acid to solids of from 0.5 : 1 to 3.5 : 1;
   iv. stirring at 15° to 80°C;
   v. separating off the insoluble pure 1,5-dinitroanthraquinone thus obtained;
   vi. adjusting the mother liquid left following separation of the crude 1,5-dinitroanthraquinone to a nitric acid concentration of from 88 to 94% for a ratio by weight of nitric acid to solids of from 3.0 : 1 to 12 : 1, with the proviso that the nitric acid concentration is at least 1.5% lower than in the preceding separation of crude 1,5-dinitroanthraquinone; and
   vii. separating off the pure 1,8-dinitroanthraquinone obtained in this way at a temperature in the range of from 20° to 50°C and freeing it from the nitric acid adhering thereto.

2. Process of claim 1 wherein the pure 1,5-dinitroanthraquinone is washed with 95 to 100% nitric acid, and then freed from the nitric acid adhering thereto.

3. Process of claim 1 wherein an nitric acid concentration of from 92.5 to 95.5% is adjusted in the separation of the 1,5-dinitroanthraquinone for a ratio by weight of nitric acid to solids of from 2.5 : 1 to 10 : 1, while a nitric acid concentration of from 88 to 92.5 is adjusted in the separation of the 1,8-dinitroanthraquinone for a ratio by weight of nitric acid to solids of from 3.5 : 1 to 10 : 1.

4. Process of claim 1 wherein a nitric acid concentration of from 94 to 96% is adjusted in the separation of the 1,5-dinitroanthraquinone for a ratio by weight of nitric acid to solids of from 5.5 : 1 to 3.5 : 1, while a nitric acid concentration of from 91 to 93% is adjusted in the separation of the 1,8-dinitroanthraquinone for a ratio by weight of nitric acid to solids of from 7 : 1 to 3.5 : 1.

5. Process of claim 1 wherein a nitric acid concentration of from 91 to 93% is adjusted in the separation of the 1,5-dinitroanthraquinone for a ratio by weight of nitric acid to solids of from 9.5 : 1 to 6.5 : 1, while a nitric acid concentration of from 88 to 91% is adjusted in the separation of the 1,8-dinioanthraquinone for a ratio by weight of nitric acid to solids of from 12 : 1 to 7 : 1.

6. Process of claim 1 wherein separation is carried out at a temperature in the range of from 20° to 35°C.

7. Process of claim 1 wherein in the separation of 1,8-dinitroanthraquinone the nitric acid concentration is adjusted by distilling off nitric acid.

8. Process of claim 1 wherein in the separation of 1,8-dinitroanthraquinone the nitric acid concentration is adjusted by adding water.

9. Process of claim 1 wherein in the separation of 1,8-dinitroanthraquinone the concentration of nitric acid is adjusted by the addition of aqueous nitric acid with a concentration of at least 65%.

10. Process of claim 1 wherein the dinitration mixture is obtained by nitrating anthraquinone and/or 1-nitroanthraquinone with nitric acid with a concentration of 94 to 100%.

11. Process of claim 10 wherein the concentrated nitric acid containing 1,5- and 1,8-dinitroanthraquinone left following separation of the pure 1,5-dinitroanthraquinone is reused for the dinitration of anthraquinone.

12. Process of claim 1 wherein the required nitric acid concentration is adjusted in the reaction mixture by distilling off concentrated nitric acid, by adding water or aqueous nitric acid or by a combination of these measures.

13. Process of claim 10 wherein the mixture of 1,5- and 1,8-dinitroanthraquinone isolated from the mother liquor left after separation of the 1,8-dinitroanthraquinone is returned to the nitration stage.

14. Process of claim 1 wherein in cases where 1,8-dinitroanthraquinone alone is separated off without previous separation of crude 1,5-dinitroanthraquinone, the dinitration mixture used contains less than 15% of 1,5-dinitroanthraquinone, and separation of the 1,8-dinitroanthraquinone is carried out with a ratio by weight of nitric acid to solids of from 3.5 : 1 to 10 : 1, with a nitric acid concentration of from 88 to 92.5% and at a temperature in the range of from 20° to 50°C.

15. Process of claim 14 wherein the dinitration mixture contains less than 10% of 1,5-dinitroanthraquinone.

16. Process of claim 14 wherein separation of the 1,8-dinitroanthraquinone is carried out at a temperature of from 25° to 35°C.

* * * * *

UNITED STATES PATENT AND TRADEMARK OFFICE
CERTIFICATE OF CORRECTION

PATENT NO. : 3,963,762
DATED : JUNE 15, 1976
INVENTOR(S) : WALTER HOHMANN

It is certified that error appears in the above-identified patent and that said Letters Patent are hereby corrected as shown below:

Column 4, line 39, after "cooling." delete "quantity.
Column 16, line 55, "fltrate" should read -- filtrate --.
Column 17, line 16, "dnitroanthraquinone" should read -- dinitroanthraquinone --.
Column 19, line 24, after "dried." insert -- 16.8 --.
Column 20, line 29, after "dinitroanthraquinone" delete the semi-colon (;).
Column 24, line 5, "quaantity" should read -- quantity --.
Column 25, line 46, "2,7%" should read -- 2.7% --.

Signed and Sealed this

Sixteenth Day of November 1976

[SEAL]

Attest:

RUTH C. MASON
Attesting Officer

C. MARSHALL DANN
Commissioner of Patents and Trademarks